United States Patent [19]

House

[11] Patent Number: 5,476,964
[45] Date of Patent: Dec. 19, 1995

[54] CONTINUOUS RACEMIZATION OF BENZYLIC ALCOHOLS, ETHERS, AND ESTERS BY SOLID ACID CATALYST

[75] Inventor: David W. House, Arlington Heights, Ill.

[73] Assignee: UOP, Des Plaines, Ill.

[21] Appl. No.: 342,460

[22] Filed: Nov. 21, 1994

[51] Int. Cl.$^6$ .................. C07C 67/02; C07C 233/00; C07C 209/00
[52] U.S. Cl. .................. 560/254; 564/165; 564/302; 564/304; 564/390
[58] Field of Search .................. 560/254; 564/165, 564/302, 304, 390, 389; 549/517

[56] References Cited

U.S. PATENT DOCUMENTS

| | | | |
|---|---|---|---|
| 5,104,899 | 4/1992 | Young et al. | 514/646 |
| 5,130,482 | 7/1992 | Takehira et al. | 564/165 |
| 5,223,646 | 6/1993 | Takehira et al. | 564/165 |
| 5,231,227 | 7/1993 | Yoneyoshi et al. | 564/390 |

OTHER PUBLICATIONS

Skrebnik, Ramachandran & Brown, *J. Org. Chem.*, 53, 2916, 1988.
Gao & Sharpless, *J. Org. Chem.*, 53, 4081, 1988.
E. J. Corey & G. A. Reichard, *Tetrahedron Letters*, 30, No. 39, 5207, 1989.
Schneider and Goergens, *Tetrahedron: Asymmetry*, No. 4, 525, 1992.

*Primary Examiner*—Arthur C. Prescott
*Attorney, Agent, or Firm*—Thomas K. McBride; Eugene I. Snyder

[57] ABSTRACT

Benzyl alcohols having a chiral center at the benzylic carbon can be conveniently racemized by treatment with solid acids which are strongly acidic cation exchange materials. Racemization may be effected generally in the range from 20°–150° C. in aqueous or partly aqueous systems in combination with a water-miscible organic solvent to improve solubility of the alcohol. Similar racemizations may be effected for benzyl ethers and esters. This process is valuable for recycling of unwanted enantiomers obtained in the resolution of racemic mixtures.

16 Claims, No Drawings

CONTINUOUS RACEMIZATION OF BENZYLIC ALCOHOLS, ETHERS, AND ESTERS BY SOLID ACID CATALYST

BACKGROUND OF THE INVENTION

It has been known for some time that for medicinals having at least one chiral center the pharmacological effectiveness of the enantiomers of the racemic mixture may differ substantially. Thus, although the recognition of the desirability of using the pharmacologically and pharmaceutically more acceptable enantiomer is old, nonetheless the use of optically pure medicinals generally is relatively new, simply because of the difficulty and cost of resolution of the racemic mixture and/or the difficulty and cost of asymmetric synthesis of the desired enantiomer. The importance of stereochemical purity may be exemplified by L-propranolol, which is known to be 100 times more potent than its D-enantiomer. Furthermore, optical purity is important since certain isomers actually may be deleterious rather than simply inert. For example, the D-enantiomer of thalidomide was a safe and effective sedative when prescribed for the control of morning sickness during pregnancy. However, L-thalidomide was discovered to be a potent teratogen leaving in its wake a multitude of infants deformed at birth.

With recent chemical advances, especially in asymmetric synthesis, has come both an increase in the feasibility of selectively preparing the more acceptable enantiomer of a given chiral medicinal, as well as increasing pressure on the pharmaceutical industry to make available only that enantiomer. An instructive example, pertinent to the subject matter of this invention, is the class of serotonin-uptake inhibitors exemplified by fluoxetine (whose racemate is available as Prozac™), tomoxetine, and nisoxetine, all of which have the structure (as the hydrochloride)

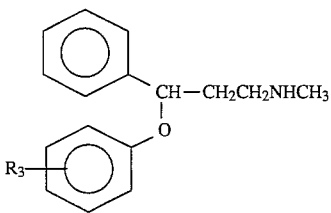

where $R_3$=4-$CF_3$, 2-$CH_3$, and 2-$C_2H_5O$, respectively.

Thus, Skrebnik, Ramachandran & Brown, *J. Org. Chem.*, 53, 2916, 1988, used chirally modified boron compounds in the asymmetric reduction of prochiral ketones. From 3-chloropropiophenone there was prepared S-3-chloro-1-phenyl-1-propanol in 97% enantiomeric purity which then was used as the starting material for the preparation of the corresponding enantiomers of S-tomoxetine and S-fluoxetine. Shortly thereafter, Gao & Sharpless, *J. Org. Chem.*, 53, 4081, 1988, developed an enantioselective synthesis of both enantiomers of tomoxetine and fluoxetine from cinnamyl alcohol via catalytic asymmetric epoxidation and regioselective reduction of the corresponding epooxycinnamyl alcohols. E. J. Corey and G. A. Reichard, *Tetrahedron Letters*, 30, No. 39, 5207 (1989) outlined a 4-step synthesis of enantiomerically pure fluoxetine from 3-chloropropiophenone in 77–82% overall yield with the key step being the enantioselective catalytic reduction of the ketone to 3-chloro-1-phenyl-1-propanol (CPP) in 99% yield and with 94% enantiomeric selectivity. Recrystallization afforded material of 100% enantiomeric purity with 82% recovery. These authors have recognized that compounds such as CPP are extremely useful in syntheses. The patentees in U.S. Pat. No. 5,104,899 recognized that the S(+)isomer of fluoxetine was the more desirable enantiomer, since it was found not to have certain side effects of the racemate such as nervousness, anxiety, insomnia, and adverse psychological effects. The patentees also recognize that the S-enantiomer had a faster onset of action with a quicker response rate.

The foregoing are examples of enantioselective synthesis. Enantioselective synthesis depends on chiral reagents of high enantiomeric purity which often are quite expensive. Consequently, another general approach is based on the efficient resolution of an early precursor, used as a raw starting material in synthesis, with high enantiomeric purity followed by subsequent conventional synthetic techniques which maintain high enantiomeric purity in intermediates through final product formation. This approach is exemplified by the work of Schneider and Goergens, *Tetrahedron: Asymmetry*, No. 4, 525, 1992. These authors effected enzymatic resolution of CCP via enzymatic hydrolysis of the racemic acetate in the presence of a lipase from Pseudomonas fluorescens under close pH control with a phosphate buffer. The hydrolysis was halted after about 50% conversion to afford the R-alcohol while leaving unchanged the S-acetate, which subsequently could be hydrolyzed with base to the S-alcohol. From the enantiomerically pure alcohols the enantiomerically pure tomoxetine, fluoxetine, and nisoxetine could be prepared.

The Schneider and Goergens approach highlights a characteristic of methods based on resolution of a racemate which requires our attention. Although in their report the authors used both the R- and S-CPP to prepare, for example, both R- and S-fluoxetine in high optical purity, when one enantiomer is substantially more desirable than the other (see U.S. Pat. No. 5,104,899, supra) in practice only the more desirable enantiomer will be utilized in subsequent synthesis. Unless one is willing to accept the economic burden of discarding the less desirable (or even undesirable) enantiomer—which is half of the starting material! - it is imperative to somehow recycle the undesired enantiomer. Stated concisely, incident to a method of preparing medicinals of high optical purity based on using a raw material of high enantiomeric purity obtained via resolution of its racemate is the requirement of recycling the unwanted enantiomer produced as a byproduct to the resolution stage. This application is directed precisely to this need to afford a cost-effective solution to the preceding problem.

SUMMARY OF THE INVENTION

The purpose of this invention is to racemized benzylic alcohols, ethers, and esters, especially in a continuous process, with high specificity and good yield. An embodiment comprises contacting an aqueous solution of a benzylic alcohol with a solid acid racemization catalyst at a temperature up to about 350° C. In a specific embodiment the catalyst is a cationic exchange material with a strong acid group. In another specific embodiment the catalyst is a cationic exchange resin and the temperature at which racemization is conducted is no greater than about 150° C. Yet another embodiment comprises contacting a solution in acetic acid of a benzyl acetate with a solid acid catalyst.

Other embodiments and purposes will become dear from the ensuing description.

DESCRIPTION OF THE INVENTION

The need for racemization of an unwanted enantiomer produced in a process of resolving a racemic mixture has been established above. The racemization must be highly specific and must effect good conversion of the enantiomer in order to recycle it to the resolution stage. What we have found is that in the class of compounds functionalized at a chiral benzylic center racemization can be effected by contacting the benzylic compound with a solid acid catalyst, especially ion exchange materials bearing strongly acidic groups, at temperatures as high as about 350° C., but generally at temperatures no greater than about 150° C. The class of compounds of interest here are alcohols, ethers, and esters; the class of solid add catalysts of particular interest in our invention are ion exchange resins, silica gels containing sulfonic add groups, and polysilsesquioxanes functionalized with strongly acidic groups.

The substrates which are being racemized in our invention have the general formula

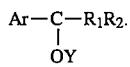

In the most important case Y=H. That is, the most important substrates to be used in the practice of an invention are benzylic alcohols having a chiral center at the hydroxyl carbon. From the foregoing it will be clear that $R_1$ must be different from $R_2$ in order that there be chirality at the benzylic carbon.

Subject to the requirement that $R_1 \neq R_2$, both $R_1$ and $R_2$ are selected from the group consisting of hydrogen and alkyl, cycloalkyl, and aromatic groups having from one to ten carbon atoms. The alkyl groups may be linear, branched, or cyclic and also may bear other substituents otherwise inert under the conditions of racemization. Representative of the groups which may be borne on an alkyl group are included halogens, hydroxyl, alkoxyl, aromatic, and amino groups, including primary, secondary, and tertiary amino groups. In a preferred mode where either or both of $R_1$ and $R_2$ are alkyl groups they contain from 1 up to about 6 carbon atoms, with or without other inert substituents. Examples of suitable groups include methyl, ethyl, propyl, butyl, pentyl, hexyl, heptyl, octyl, nonyl, and decyl. Other suitable groups include chloromethyl, bromoethyl, hydroxypropyl, methoxybutyl, aminopropyl, chloroethyl, aminoethyl, methylaminoethyl, ethoxypentyl, phenyl, and so forth. The aforementioned materials are merely representative of those which can be used as $R_1$ and $R_2$ but do not exhaust materials suitable in the substrates being racemized.

The group Ar represents an aryl group, chief of which is the phenyl group, $C_6H_5$. Other representative aryl groups include naphthyl, anthryl, phenanthryl, pyridyl, and so forth. The aryl group also may be substituted by other inert substituents, especially in the case of a substituted phenyl group. Suitable substituents on the aryl ring include alkyl groups having from 1 through 6 carbon atoms, and other groupings inert under racemization conditions such as halogen, hydroxyl, alkoxyl, and so forth. As examples of benzylic alcohols having a chiral benzylic carbon atom which may be used in the practice of our invention may be mentioned 1-phenylethanol, 1-phenyl-1-propanol, 1-phenyl-1-butanol, 2-phenyl-2-butanol, 2-phenyl-2-pentanol, 3-chloro-1-phenyl-1-propanol, 3-chloro-1-phenyl-1-butanol, 4-bromo-1-phenyl-1-butanol, 4-bromo-2-phenyl-2-butanol, 3-methylamino-1-phenyl-1-propanol, 1-tolylethanol, 1-(trifluoroethylphenyl)-1-propanol, 3-chloro-1-(methoxyphenyl)-1-propanol, 1-(trichloromethylphenyl)-1-propanol, 1-hydroxyphenyl-2-methyl-1-propanol, and so forth.

The foregoing description of substrates has been that of suitable benzylic alcohols. Analogous benzylic ethers and esters also may be used in the practice of our invention. That is, Y may be an alkyl group (to afford benzylic ethers) or a carboalkyl group (to afford the corresponding benzyl esters), i.e., Y=$R_3$ or $C(O)R_3$, where $R_3$ is a lower alkyl group containing from I to 6 carbon atoms. Aromatic ethers also may be used, i.e., Y=Ar, especially where the aryl group is a phenyl or substituted phenyl group. Examples of suitable alkyl groups which may be used as ethers or as esters include those from the foregoing list illustrating the nature of $R_1$ and $R_2$. Specific examples of carboalkyl groups which may be used in the esters of our invention include $CH_3C(O)$—, $ClCH_2C(O)$—, $Cl_2CHC(O)$—, $CF_3CH_2C(O)$—, $C_6H_5C(O)$— and substituted benzoates where the substituent is an alkyl, halogen, alkoxy, or hydroxy group. Examples of aryl ethers which may be used in the practice of our invention (i.e., Y=Ar) includes $C_6H_5$, the corresponding phenyl group substituted by an alkyl, halogen, or alkoxy group, among which may be mentioned chlorophenyl, methylphenyl (tolyl), trifluoromethylphenyl, ethylphenyl, trifluoroethylphenyl, methoxyphenyl, 2,2,2-trifluoroethoxyphenyl, and so on.

The racemization process itself is effected by contacting a solution of the benzylic substrate with a solid acid as the racemization catalyst at temperatures between room temperature (ca. 20° C.) and up to as high as about 350° C. More particularly, contacting is done with a strong acid cation exchange material at temperatures up to about 150° C. for as short a contact time as possible. It has been observed that dehydrogenation of the alcohols of our invention to olefins is favored by higher temperatures and longer contact times, consequently there is a strong interest in keeping temperatures as low as possible and contact times as short as possible.

We have found that strong ion exchange materials bearing sulfonic acid groups are particularly effective as racemization catalysts. Chief among these are strong acid cationic exchange resins such as Dowex™ 50W-X8, Dowex™ 50X8-100, the Amberlyst™ resins 15, 18, 31, 32, 36, XN-1010, XE-365, IR-120 PLUS(H), Duolite™ C-25D, the Purolite™ resins MN400, CT-175, S940 ($Na^+$), S950 (Na+), and CT 165 DR. This class also includes fluorinated alkyl sulfonic acid groups on resins such as Nafion™. Another class of solid add catalysts which may be used in the practice of our invention are silica gels with sulfonic acid groupings which contain sulfonic acid groups covalently bonded to a silica gel support via organosilane linkages, as represented by Deloxan™ ASP ⅐ from Degussa Corp. Yet another group of effective solid acid catalysts in racemization are polysilsesquioxanes beating strong acid groups as are described in application Ser. No. 08/149,391.

The major competing reaction accompanying racemization is dehydration as exemplified by

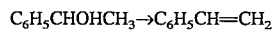

Olefin formation may be minimized by effecting racemization at as low a temperature as possible and also using as a solvent HOY. That is, where racemization of alcohols are being effected it is preferred that the racemization be performed in the presence of as high a water concentration as possible. Where an ether is being racemized it is preferred that the ether be in a solution of its corresponding alcohol HOY. Similarly, where esters are being racemized it is preferred that racemization be done in a solution of the corresponding carboxylic acid.

It is common to effect the racemization in solution rather than using a neat substrate. For alcohols, an aqueous solution is best, and preferred organic cosolvents are those which are miscible with water. Exemplary of these are dipolar aprotic materials such as tetrahydrofuran, dioxane, dimethylsulfoxide, acetonitrile, the various glymes (diethers of polyethyleneglycol), dimethylformamide, hexamethylphosphoramide, and so forth. Where ethers are being racemized (Y=alkyl, aryl, and so forth) it is preferred that the solution be in an alcohol which corresponds to the ether functionality, either alone or in admixture with an otherwise inert solvent such as those listed above. Finally, where esters are racemized (Y=carboalkyl or carboaryl) it is preferred that the substrate be dissolved in a suitable carboxylic acid as solvent.

Although racemization may be effected in either a batch or continuous mode it is much preferable that the process be carried out continuously. Thus, the solid acid catalyst effective in racemizing the substrates of our invention is used most conveniently as a packed bed. A solution of the substrates of our invention then will be flowed through the mass of solid acid catalyst either in a downflow or an upflow mode. Bed temperatures will vary between ambient, i.e., about 20° C., up to as high as about 350° C. depending upon the nature of the solid acid catalyst in the packed bed as well as the substrate undergoing racemization. However, because of the nature of materials where the packed bed consists of an ion exchange resin and because of the desire to work at as low a temperature as is consistent with racemization, temperatures no greater than about 150° C. are preferred. Contact times are kept as short as possible in order to minimize side reactions.

The following examples are merely illustrative of our invention and are not intended to limit it in any way thereby.

EXAMPLE 1

Racemization of R-(+)-Phenylethanol. Into a 50 mL, three-necked, round bottomed flask equipped with a reflux condenser, a thermometer (attached to a temperature controller and a heating mantle), and containing a Teflon-coated stirring star, were added 0.25 g (0.002046 mol) of R-(+)-phenylethanol, 25.0 g of water, and 0.50 g of Amberlyst® 15. Amberlyst® 15 is a strongly acidic, macroreticular ion-exchange resin from Rohm and Haas.

The reaction slurry was heated to 65° C. with vigorous stirring. The progress of the racemization was followed using a Perkin-Elmer Model 241 polarimeter. The stability of the alcohol was followed using high performance liquid chromatography. Over a period of about 4.3 hours, the optical rotation of the reaction solution dropped from +0.350° to 0.003° which is within the uncertainty of the polarimeter. The reaction solution at the start and end of the racemization was clear and colorless. A small amount of styrene was detected using high performance liquid chromatography and a UV (254 nm) detector. However, the amount of styrene was not sufficient to appear in the refractive index detector; hence it was present in less than 0.1%. No other side-products were detected.

The initial solution of R-(+)-phenylethanol (Aldrich Chemical Co.) in water, without catalyst present, had a specific rotation of +36.1° at 2.3° C. This number was used as the rotation for the optically pure R-(+)-phenylethanol in water. Time 0 in Table 1 was recorded after the reaction mixture had reached 65° C., by which time some racemization already had occurred.

TABLE 1

Polarimetric Data for the Racemization of R-(+)-Phenylethanol in Water over Amberlyst ™ 15 at 65° C.

| Time, Hours | Observed Rotation | R-(+), % | S-(−), % |
|---|---|---|---|
| 0 | +0.350 | 98 | 2 |
| 0.43 | +0.315 | 94 | 6 |
| 0.70 | +0.232 | 82 | 18 |
| 0.95 | +0.174 | 74 | 26 |
| 1.20 | +0.130 | 68 | 32 |
| 1.45 | +0.097 | 63 | 37 |
| 1.70 | +0.073 | 60 | 40 |
| 2.20 | +0.042 | 56 | 44 |
| 2.75 | +0.022 | 53 | 47 |
| 3.28 | +0.011 | 52 | 48 |
| 3.80 | +0.006 | 51 | 49 |
| 4.30 | +0.003 | 50 | 50 |

EXAMPLE 2

Continuous Racemization of S-(−)-3-Chloro-1-phenyl-1-propanol. The continuous racemization of S-(−)-3-chloro-1-phenyl-1-propanol was carried out in a bench-scale, fixed-bed microreactor with a bed volume of 5.0 mL. A pulseless liquid chromatography pump was used to deliver the feed at a rate of 2.0 LHSV. The temperature of the reactor bed was controlled using a programmable temperature controller. The temperature of the reaction was ramped from 75° to 225° C. in increments of 25° C. with 2 hour dwells at each increment.

The feed was prepared by dissolving 2.52 g of S-(−)-3-chloro-1-phenyl-1-propanol (3-CPP) in 180.0 g of a 50/50 blend of water and n-propanol. The catalyst used was Deloxan™ ASP (Degussa), which is a macroporous organofunctional polysiloxane, strongly acidic support with chemically-bonded sulfonic acid groups at 0.7–1.1 meq/g dry, 0.1–0.4 mm diameter particles, and density about 2.0 g/mL. The progress of the racemization was followed using liquid chromatography with a chiral column, (R,R)-Whelk-O 1, from Regis Technologies, Inc. The ratio of each enantiomer present at any given temperature (based on area counts from a UV detector set at 254 nm) is shown in Table 2.

TABLE 2

Continuous Racemization of S-(−)-3-chloro-1-phenyl-1-propanol in a Fixed-bed Microreactor: Percent Enantiomer vs. Temperature.

| Reactor Temp, °C. | Ratio | | 3-CPP, % |
|---|---|---|---|
| | R-(+)-enantiomer | S-(−)-enantiomer | |
| 78 | 0 | 100 | 100 |
| 103 | 0.2 | 99.8 | 98 |
| 129 | 8.3 | 91.7 | 93 |
| 155 | 37.8 | 62.2 | 66 |
| 179 | 33.4 | 66.6 | 21 |
| 204 | 0 | 0 | 0 |

The fourth column in the table shows that the total amount of 3-CPP is going down with increased temperature due to alkylation of 3-CPP by n-propanol. At lower temperatures, this solvent does not present much of a problem; however, at higher temperatures, the competition becomes significant. The n-propanol is used as a co-solvent due to the insolubility of 3-CPP in pure water. More inert solvents with similar solubility characteristics to n-propanol would circumvent the competition with alkylation.

What is claimed is:

1. A process for the continuous racemization of an enantiomer of a compound of formula

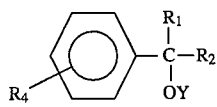

where $R_1$ and $R_2$ are dissimilar and are selected from the group consisting of hydrogen, alkyl, cycloalkyl, and aromatic groups containing from 1 up through about 10 carbon atoms, and haloalkyl, alkoxyalkyl, and aminoalkyl groups containing from 1 up to about 10 carbon atoms; Y is selected from the group consisting of hydrogen, lower alkyl containing up to about 6 carbon atoms, aryl, and carboalkyl groups containing up to about 7 carbon atoms; and $R_4$ is selected from the group consisting of hydrogen lower alkyl having up to about 6 carbon atoms, halo, hydroxy, and alkoxy groups comprising flowing said enantiomer, at racemization conditions effective to racemize the enantiomer, through a mass of a solid acid which is a strongly acidic ion exchange material.

2. The process of claim 1 where Y is hydrogen.

3. The process of claim 1 where Y and $R_1$ are hydrogen and $R_2$ is $ClCH_2CH_2$.

4. The process of claim 1 where the racemization conditions include a temperature between about 20° and about 350° C.

5. The process of claim 1 where the strongly acidic ion exchange material is selected from the group consisting of cation exchange resins, silica gel having bonded sulfonic acid groups, and polysilsesquioxanes having strong acid groups.

6. The process of claim 5 where the strongly acidic ion exchange material is a cation exchange resin bearing sulfonic acid groups.

7. The process of claim 6 where the racemization is conducted at a temperature from about 20° up to about 150° C.

8. The process of claim 1 where Y is $C(O)CH_3$, $R_4$ is hydrogen, $R_1$ is H, and $R_2$ is $ClCH_2CH_2$.

9. The process of claim 1 where Y is an aryl group.

10. The process of claim 1 where the aryl group of Y is phenyl, (trifluoromethyl)phenyl, methylphenyl, or alkoxyphenyl where the alkoxy group has from 1 through 6 carbon atoms.

11. A process for the continuous racemization of an enantiomer of an alcohol of formula

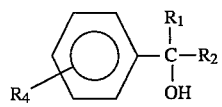

where $R_1$ and $R_2$ are dissimilar and are selected from the group consisting of hydrogen, alkyl, cycloalkyl, and aromatic groups containing from 1 up through about 10 carbon atoms, and haloalkyl, alkoxyalkyl, and aminoalkyl groups containing from 1 up to about 10 carbon atoms, and $R_6$ is selected from the group consisting of lower alkyl having up to about 6 carbon atoms, halo, hydroxy, and alkoxy groups, comprising flowing said alcohol enantiomer, at racemization conditions effective to racemize said enantiomer, through a mass of a solid acid which is a strongly acidic ion exchange material.

12. The process of claim 11 where $R_1$, is hydrogen and $R_2$ is $ClCH_2CH_2$.

13. The process of claim 11 where the racemization conditions include a temperature between about 20° and about 350° C.

14. The process of claim 11 where the strongly acidic ion exchange material is selected from the group consisting of cation exchange resins, silica gel having bonded sulfonic acid groups, and polysilsesquioxanes having strong acid groups.

15. The process of claim 14 where the strongly acidic ion exchange material is a cation exchange resin bearing sulfonic acid groups.

16. The process of claim 15 where the racemization is conducted at a temperature from about 20° up to about 150° C.

* * * * *